United States Patent [19]

Austin

[11] Patent Number: Plant 7,220

[45] Date of Patent: Apr. 17, 1990

[54] ROSE PLANT NAMED 'AUSBOARD'

[76] Inventor: David C. H. Austin, Bowling Green Farm, Bowling Green Lane, Albrighton, Wolverhampton, England

[21] Appl. No.: 259,278

[22] Filed: Oct. 18, 1988

[51] Int. Cl.[4] ..... A01H 5/00

[52] U.S. Cl. ..... Plt./1

[58] Field of Search ..... Plt. 1, 11

*Primary Examiner*—James R. Feyrer

*Attorney, Agent, or Firm*—Ladas & Parry

[57] ABSTRACT

A new variety of rose plant of the shrub class distinctive in its character by its fully double, deep pink flowers with abundant, continual blooming and the unusual blend of coloring and shaping of the flower.

1 Drawing Sheet

BACKGROUND OF THE INVENTION

The present invention relates to a new and distinct variety of shrub rose, a seedling resulting from a definite effort to produce an improvement in this class of roses.

Primary features of this new variety which connote a distinctive advance over existing types are the vigorous abundant and continual blooming taken with the perfection of the fully double flowers of an old-fashioned type more particularly apparent in the accompanying illustration of a sepcimen thereof.

BRIEF DESCRIPTION OF DRAWING

The drawing depicts, from side view, stems, foilage, flower buds and flowers in various stages of developments.

DETAILED BOTANICAL DESCRIPTION

The following is a detailed description of the new variety, colour terminology being in accordance with the "Methuen Handbook of Colour" published by Eyre Methuen Ltd. (1963).

Variety Denomination (in accordance with the UPOV Convention): Ausbord (Trade name Gertrude Jekyll).

Type: Hardy; bush; outdoor; seedling; for cut flowers and garden decoration.

Class: shrub

Propagation: holds its distinguishing characteristics through succeeding propagations by budding.

The rose plant was grown at Albrighton, Nr. Wolverhampton, England and was derived as follows:

Female parent (seed parent): An unnamed seedling.

Male parent (pollen parent): Comte de Chambord.

The operation of the artificial pollination is therefore expressed by the following (Seedling×Comte de Chambord).

The following observations are made of specimens grown outdoors in England.

Plant Description

Plant:

*Height.*—120–150 cm.

*Habit.*—Tall, strong, shrubby.

Branches:

*Colour.*—Young stems: Medium to Dark Green 3 F8. Adult wood: Dark Green 29 F8.

Leaves:

*Stipules.*—Broad, Medium Green tinged with red. Serrated edge with glandular hairs. Long wings at end.

*Petiol.*—Upper side — Concave, Green with a tint of Red. Glandular hairs at edges. Under side — Convex, Light Green, occasional glandular hairs. Very occasional prickles.

*Folioles.*—Number 3, 5 most common 6. Shape — ovate with rounded tip. Serration — dentate. Texture — Medium — slightly rugulose.

*General effect.*—Fairly dense Dark Green, matt.

*Colour.*—Young foilage — Upper side — Medium Green 30 D8, tinged red. Under side — Colour 10 E7 turning Red. Adult foilage — Upper side — Dark Green 28 F8. Under Side — Deep Green 30 E8 tinged Red.

Hips and seeds: This variety does not produce seeds in all gardening conditions, only when cross-pollinated.

Inflorescence

Number of flowers: Solitary.

Peduncle: Straight, Rigid, Medium to Light Green tinged Red with aciculas.

Length: 8 cm on average.

Sepals:

*Upper side.*—Relatively narrow. Medium Green, finely hairy.

*Under side.*—Medium Green, sparsely hairy with glandular hairs and sometimes very narrow lobes.

Bud:

*Shape.*—Oval, pointed.

*Length.*—3 cm. on average.

*Size.*—Small to medium.

*Colour.*—When opening. Upper side: Light Yellow 1 B7 at base, turning to Deep Pink 11 C8. Under side: As above.

Flower:

*Shape.*—Slightly flattened cup.

*Diameter.*—11 cm on average.

*Colour.*—When opening. Upper side: Yellow at base turning to Red 1 A8 to 12 A7. Under side: Same as above. When blooming: Upper side — Yellow at base turning to Deep Pink 1 A8 to 13 B4. Under side — Yellow at Base turning to Light Red 1 Deep Pink — 1 A8 to 13 B6. When finished blooming: Upper side: Light Red/Deep Pink paling to outisde 13 B6. Under side: Deep Rose Pink 13 B4.

Fragrance: Strong old rose fragrance.

Lasting quality: Long.

Petals:

*Shape.*—Ovate.

*Texture.*—Silky.

*Number.*—84 on average.

*Cleaning.*—Good.

Reproductive Organs

Stamens:

*Number.*—69 on average.

*Anthers.*—Pale Yellow.

*Filaments.*—Yellow.

Pistils:

*Number.*—68 on average.

*Stigmas.*—Straw.

*Styles.*—White — irregular heights.

*Receptacle.*—Pale Green shallow cup through longitudinal section.

The Development:

*Vegetation.*—Vigorous.

*Blooming.*—Continual.

*Aptitude to bear fruits.*—Normal.

*Resistance to frost.*—Good.

*Resistance to diseases.*—Good.

I claim:

1. A new and distinct variety of rose plant of the shrub class, characterized as to novelty by its fully double, deep pink flowers with abundant and continual blooming the unusual blend of coloring and shaping of the flower being substantially as shown and described.

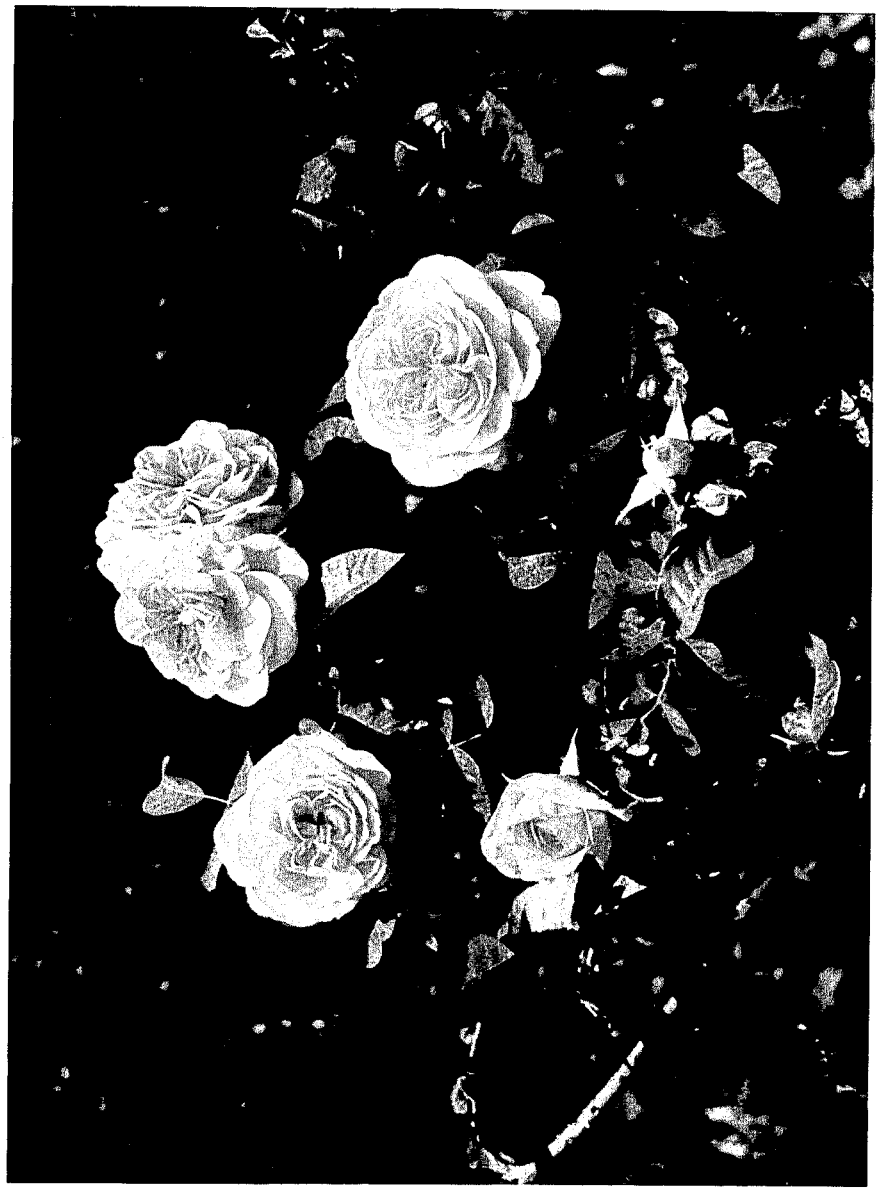

* * * * *